United States Patent [19]

Yokoyama et al.

[11] Patent Number: 6,090,983
[45] Date of Patent: Jul. 18, 2000

[54] MATTER OF COMPOSITION AND METHOD FOR USING THE SAME AS PLANT BIOREGULATORS

[75] Inventors: Henry Yokoyama; James H. Keithly, both of Pasadena, Calif.; Harold W. Gausman, Amarillo, Tex.

[73] Assignees: Tropicana Products, Inc., Bradenton, Fla.; The United States of America as represented by the Secretary of Agriculture, Washington, D.C.

[21] Appl. No.: 08/203,386

[22] Filed: Mar. 1, 1994

Related U.S. Application Data

[62] Division of application No. 07/860,413, Mar. 30, 1992, Pat. No. 5,298,483.

[51] Int. Cl.[7] .................................................. C07C 217/10
[52] U.S. Cl. ............................................................ 564/346
[58] Field of Search ............................................ 564/346

[56] References Cited

U.S. PATENT DOCUMENTS 2,766,238  10/1956  Felton ................................. 260/247.7
3,558,640  1/1971  Shen et al. ........................... 260/294.8

FOREIGN PATENT DOCUMENTS 1239567  7/1971  United Kingdom .

*Primary Examiner*—S. Mark Clardy
*Attorney, Agent, or Firm*—Cook, Alex, McFarron, Manzo, Cummings & Mehler, Ltd.

[57] ABSTRACT

The present invention is directed to a new matter of composition in the form of chemical compounds and to a method for enhancing plant growth and the properties exhibited by plants treated with the compounds in accordance with this method. In particular, application of the compounds results in an increase in sugar content, essential oils and proteins along with an increase in total plant biomass. Fruits harvested from treated plants exhibit an accelerated biochemical and structural maturity. Citrus fruits typically show a reduced peel thickness and exhibit significant improvements in vitamin C, carotenoid, and essential oil contents. The methods of the present invention produce balanced improvements in the structural, biochemical, and sensory quality of Citrus fruits.

2 Claims, 3 Drawing Sheets

MATTER OF COMPOSITION AND METHOD FOR USING THE SAME AS PLANT BIOREGULATORS

This application is a division of application Ser. No. 07/860,413, filed Mar. 30, 1992, now U.S. Pat. No. 5,298,483.

FIELD OF INVENTION

The present invention is directed to a new matter of composition in the form of chemical compounds and to a method for enhancing plant growth and the properties exhibited by plants treated with the compounds in accordance with this method. In particular, application of the compounds results in an increase in sugar content, essential oils and proteins along with an increase in total plant biomass. Fruits harvested from treated plants exhibit an accelerated biochemical and structural maturity. Mature fruits typically exhibit improved pigment and essential oil accumulation, and reduced peel thickness.

It has been discovered that the new class of compounds function as plant bioregulators and thus enhance plant growth in accordance with the method of the invention.

BACKGROUND OF THE INVENTION

Developments in agriculture have produced chemical compounds and methods for their application which function as plant bioregulators and thus serve to enhance one or more properties exhibited by the treated plant. For example, U.S. Pat. No. 3,671,219 discloses a quarternary ammonium compound which when applied to plants enhances the sugar content of sugar cane. U.S. Pat. No. 4,204,859 discloses that the addition of certain phenoxytrialkylamines enhance the hydrocarbon production of rubber in plants. U.S. Pat. No. 4,159,903 discloses a method for increase of polyisoprene production in rubber producing plants such as Guayule. U.S. Pat. No. 3,833,350 discloses that carotenoid accumulation in plants can be increased according to a method comprised of applying compounds including (halogenated phenoxy) tri-alkylamines. U.S. Pat. Nos. 3,864,501, 3,911,148, and 3,911,152 disclose a method for increasing the carotenoid pigments of fruits and vegetables which comprises the application of compounds including (methyl phenoxy) tri-alkylamines.

U.S. Pat. No. 4,797,153 discloses a method for increasing total plant biomass and individual plant constituents such as sugar, protein, lipid, and essential oils which comprises the application of certain substituted phenoxytrialkylamines and substituted phenylthiotrialkyl amines, or dialkylmorpholium halides. The compounds are applied in bioregulatory amounts to plant seeds, plant seedlings, or plant buds at the early stage of plant development, or to trees during a week before or after flower bud swell. It has since been shown that the application of the compounds of this reference in bio-regulatory amounts effect the photosynthetic pathway in green plants in a manner which facilitates the assimilation of carbon dioxide in the photosynthetic pathway, thereby increasing the carbon atoms available for synthesis of total biomass and individual plant constituents.

SUMMARY OF THE INVENTION

The present invention is directed towards a new class of (benzyl substituted) trialkylamine ether compounds which when applied to plants in regulatory amounts increase important plant constituents, increase total plant biomass, and increase the rate of plant growth, and reduce the time to crop maturity. Pigment accumulation in plant leaves and mature fruits is increased. In Citrus crops, the fruits harvested from treated trees exhibit a reduced peel thickness. The compounds are applied to the plants in bioregulatory amounts—that is, an amount sufficient to increase plant biomass and accelerate growth but insufficient to harm the plant. The compounds of the present invention are selected from the group of chemical compounds having the structure:

wherein X is either oxygen or sulfur, $R_1$ and $R_2$ are lower alkyl groups containing 1 to 6 carbon atoms each of identical or dissimilar structure, $n_1$ and $n_2$ are integers from 1 to 6, with $n_1$ and $n_2$ being independent. of each other, $R_3$ and $R_4$ are independently hydrogen, chlorine, bromine, fluorine, lower alkyl compounds containing 1 to 6 carbon atoms, lower alkoxy containing 1 to 6 carbon atoms, or condensed mono- and polycyclic aromatic ring systems, and wherein:

if $R_3$ and $R_4$ are 3,5-substituents, then the lower alkyl or alkoxy group must contain 1 to 6 carbon atoms; and wherein: if $R_3$ is hydrogen, then $R_4$ must be a 4-substituent, with the proviso that $R_4$ is other than hydrogen; or b) an acid addition salt of the compounds defined above.

It has been found that the application of the compounds of the invention causes the treated plants to form and store valuable plant constituents over untreated plants. The plants which have been treated with the bioregulatory compounds of the invention have greater biomass than untreated plants resulting in increased crop production per unit area.

Moreover, it has found that in field studies conducted wherein the compounds of the present invention are compared with the bioregulator compounds disclosed in U.S. Pat. No. 4,797,153, specifically 3,4-dichlorophenoxy tri-ethylamine (3,4-DCPTA), 2,4-dichlorophenoxytriethylamine, (2,4-DCPTA), it was determined that a compound of the present invention known as N,N-diethylaminoethyl (4-methylbenzyl) ether (MBTA) is generally more effective as a plant bioregulator than the bioregulator compounds disclosed in the '153 patent, That is, MBTA treated plants exhibit a greater increase in total plant biomass and valuable plant constituents relative to DCPTA. A second compound of the invention, N,N-diethylamino ethyl 3,4-dichlorobenzyl ether (DCBTA) performs comparably as a bioregulator with respect to the DCPTA. Thus, the compounds of the present invention exhibit a structure-activity correlation at least comparable and even superior to the disclosed prior art and thus represent an advance in the state of the art of bioregulator applications.

In many cases the invention increases the growth rate of the treated plant relative to untreated plants, resulting in accelerated maturation. Shorter growing periods effect a decrease in the labor and cost of production, effect a decrease in the use of energy sources such as fossil fuel which are used in fertilizer production. Moreover, accelerated and increased growth make likely the possibility that growing cycles will be shorter while yielding a harvest equivalent or superior to that of untreated plants. Such a harvest would be greater since the treated plants exhibit increased biomass. It is even conceivable that multiple harvests can be achieved within growing cycles which yield only one harvest. These possibilities offer promise for increased food productions at reduced costs and may possibly alleviate food shortages throughout the world.

DETAILED DESCRIPTION OF THE PREFERRED EMBODIMENT

The benefits of the invention are obtained by applying any of the following compounds to leaves, to plant seeds, seedling plant buds or immature fruits. Examples, by way of illustration and not limitation, of compounds that can be used in the process of the invention are:

A. N,N-dialkylaminoalkyl 2,4-substituted benzyl ethers wherein the 2,4-substituents are independently chloro, bromo, iodo, methyl, ethyl, propyl, butyl, pentyl, hexyl, methoxy, ethoxy, propoxy, butoxy, pentoxy or hexoxy, and wherein the alkyl and dialkyl groups are independently either methyl, ethyl, propyl, butyl or pentyl or isomers thereof.

B. N,N-dialkylaminoalkyl 3,5-substituted benzyl ethers wherein the 3,5-substituents are independently chloro, bromo, iodo, methyl, ethyl, propyl, butyl, pentyl, hexyl, propoxy, butoxy, pentoxy or hexoxy, and wherein the alkyl and dialkyl groups are the same as those in A.

C. N,N-dialkylaminoalkyl 3,4-substituted benzyl ethers wherein the 3,4-substituents are independently chloro, bromo, iodo, methyl, ethyl, propyl, butyl, pentyl, hexyl, methoxy, ethoxy, proproxy, butoxy, pentoxy or hexoxy, and wherein the alkyl and dialkyl groups are the same as those in A.

D. N,N-dialkylaminoalkyl 4-substituted benzyl ether wherein the 4-substituent is either methyl, ethyl, propyl, butyl, pentyl, hexyl, methoxy, ethoxy, propoxy, butoxy, pentoxy or hexoxy, and wherein the alkyl and dialkyl groups are the same as those in A.

E. N,N-dialkylaminoalkyl (substituted naphthyl) ether wherein the alkyl and dialkyl groups are the same as those in A.

The preferred compounds of the present invention as set forth in groups A through E are those where $n_1$ is 1 and $n_2$ is 2, X is oxygen, the N,N-dialkyl groups are dimethyl, the alkyl group is ethyl, and the benzyl substituents are 2,4-dichloro; 3,4-dichloro; 3-5-diisopropyl; 3,5,-ditertiary butyl; 3,4-dimethyl; 3,4-dimethoxy; 3-methyl, 4-methyl, 4-chloro or 3,4-naphthoxy.

It has been found that two particular compounds are especially preferred in that plants treated therewith exhibit significant improvements in total plant biomass and individual plant constituents, and in particular compare favorably to the bioregulator compounds disclosed in the U.S. Pat. No. 4,797,153. These compounds are N,N-diethylaminoethyl 3,4-dichlorobenzyl ether (DCBTA) and N,N-diethylaminoethyl 4-methylbenzyl ether (MBTA).

Various acid addition salts of the above compounds are readily produced. For example, by adding acid to the compounds of this invention, the following acid addition salts are formed:

Wherein the molecular constituents are as set forth above, and wherein A is the anion derived from the acid added to the amine to form a salt.

In order to achieve increase in total biomass yield, enhancement of individual plant constituents or increase in rate of plant growth, the compounds of the invention must be first applied to the plant at an early stage of development, that is, immediately prior to, or at the time when cell differentiation and plant growth are great. If application is made at a late stage of development some increase in yield or plant constituents may occur but not the significant increase which occurs where treatment is earlier. As a practical matter, treatment is made to the seed; to the post-emergent seedling plant, that is, to the plant at or prior to the full expansion of the fourth set of primary leaves, such as at the cotyledon, true leaf, two-leaf or four-leaf stage; or to trees during flower bud swell or a week before or after. For plants which are not grown from seed or do not produce flower buds such as vegetatively propagated plants like sugarcane, application should be at the developmental growth stages equivalent to the ones aforementioned. Since growth of the plant or tree dilutes the concentration of the bioregulatory compound due to increase in plant biomass resulting in a biomass dilution effect, it may be desirable to apply more than one application subsequent to the initial one. Subsequent applications should be made before completion of cell differentiation of the growing plant or when applied to a growing tree before the completion of cell differentiation of the growing fruit.

The effective amount of the compound to be applied so as to achieve the increase in biomass contemplated by the invention varies depending upon the stage of the plant's development when application is made, on whether the plant is grown in the field or greenhouse, the degree of penetration of the plant by the bioregulator, and whether or not a penetrating agent is used.

Generally, where the compounds are applied to the seeds, the concentration is about 0.001 to 0.3 mg of active ingredient per seed. Application is conveniently made by dissolving the compound to be used in water at a concentration of 0.1 to 50 parts per million (ppm) in the diluent and soaking the seeds for 2 to 6 hours. Other means of treatment of seeds such as encapsulation of the seeds with the compounds by conventional methods are encompassed by the invention.

When application is made to the seedling, that is at the cotyledon, true leaf, two-leaf or four-leaf stages and the like the treatment is about 0.001 mg to 0.3 mg active ingredient per plant. This can be accomplished by using a treatment rate of about 0.1 to 200 ppm and preferably 5 to 120 ppm. Use of treatment rates of 300 ppm or greater on young seedlings or young plants, that is prior to the full expansion of the fourth set of primary leaves, will either not cause increases in biomass contemplated by the invention or in many cases, may have a phytotoxic effect on the plant causing it to have stunted growth.

Treatment of perennial trees requires a greater amount of the bioregulator compound due to the greater mass of the tree. Generally, about one to four grams active ingredient per tree is applied using a treatment rate of 0.1 to 500 ppm of bioregulatory compound.

The compounds of the invention may be applied to the plant in any convenient manner. For example, the compound after being dissolved in water, can be sprayed onto the branches and leaves of the plant. Other application techniques known to the skilled artisan may be employed.

Appropriate wetting agents such as Triton X-100 (polyethylene glycol p-isooctylphenylether made by J. T. Baker), ORTHO X-77 (a mixture of fatty acids, fatty alcohols and isopropanol made by Chevron Chemical company), sweep 4F (chlorothalonil from Diamond Shamrock Company) and the like may be added to the aqueous solution to aid in plant treatment. Appropriate penetrating agents such as B-cyclodextrin (B-(heptamer)-cyclodextrin made by Takeda Chemical Industries, Ltd.) or Tween 80 (polyoxyethylene (20) sorbitan monooleate, available from E. Merck, Darmstadt Germany) may be added to the aqueous solution to increase penetration of the bioregulatory compound. Solutions of bioregulator and appropriate wetting agent may be adjusted to an acidic pH (pH 4 to 5) prior to plant application. However, the addition of wetting agent (s) or adjustment of the final bioregulator solution to a specified pH value does not limit the scope of the invention.

Without any intention of limiting the scope of the invention, it is theorized that the compounds used in the method of the invention play a role in the photosynthetic pathway in green plants. It is theorized that application of the compounds to the developing green plant causes increased assimilation of carbon dioxide in the photosynthetic pathway thereby increasing the carbon atoms available for synthesis of total biomass and individual plant constituents. It is further theorized that use of the compounds at an early stage of plant or fruit development and before completion of cell differentiation enhances the genetic expression of the plant so as to tap unused biological potential. Thus as new cells develop under the influence of the bioregulatory compounds, they possess increased capacity to form and store valuable materials and to form increased amount of plant tissues.

As stated above, the compounds of the invention when applied in accordance with the method of the invention, substantially increase total biomass, enhance the amount of some or all plant constituents and in many cases increase the rate of growth in green plants over untreated plants as long as constituents such as water and light which are necessary for plant growth are present in the required amount.

Using the method of invention, seed treatment of radish resulted in a greatly enhanced root and leaf development at crop harvest as compared with controls. Seed or foliar treatment of petunia, verbena, aster, and other ornamental crops increased root development, secondary branching and increased bud count per plant. Treated ornamental crops typically flower sooner and have a greatly improved aesthetic appeal. Treatment of Citrus trees causes the fruit to mature faster, to bear an increased fruit yield, to increase the Vitamin C content and to produce fruits with an increased essential oil content. USDA color score values of juiced recovered from treated Citrus is superior due to an increased pigment content. Thus, the method of the invention finds use on any green plant where increased rate of growth, biomass or the like is desired. The method is particularly valuable for use on plants which produce food, vitamins, nutrients, fiber, or energy; or on plants where commercial production is limited due to low plant yield when grown without bioregulators. The composition and method can be used on annual or perennial plants, such as seasonal roll crops, vineyards, orchards, and all ornamental or horticultural plants.

EXAMPLE 1

Two year old grafted trees of 'Okitsu-wase' Satsuma mandarin as well as two year old "Kara" and "Kinnow" grafted trees were planted into 25 liter pots and were maintained under 40% saran cover in Pasadena, Calif. The following tertiary amines were prepared as 100 ppm solutions (pH 5.0) in 0.5% Tween 80 (v/v):

N,N-diethylaminoethyl 3,4-dichlorophenylether (DCPTA) (a/k/a (3,4-dichlorophenoxy) trialkylamine)

N,N-diethylaminoethyl 3,4-dichlorobenzylether (DCBTA)

N,N-diethylaminoethyl hexanoate (HTA)

The bioregulator solutions were applied to foliage runoff in a single application. Each treatment group contained two trees. Control trees were sprayed to foliage runoff using 0.5% Tween 80 (v/v). At the time of bioregulator application, Satsuma fruit diameters ranged from 0.8 to 1.4 cm. During fruit development, the trees were fertilized every 14 days using a 20N-20P-20K soluble fertilizer and the trees received a monthly side-dressing of Ironite. Mature Satsuma fruits were harvested at 7 months after bioregulator application. In each bioregulator treatment group, mature fruits from the two replicate trees were combined for fruit quality analysis. For analysis, five fruits of approximately 50 to 55 mm in diameter were chosen from each treatment group. Total fruit fresh weight was determined. Fruits were cut in half and peel thickness was determined. Fruits were juiced by hand. The combined juice and pulp were pressed through a 0.5 mm sieve and the final juice volume and juice fresh weight were determined. Peel fresh weight after juicing and pulp fresh weight were determined. Samples of juice were centrifuged at 27,000×g for 10 minutes. The supernatants were decanted and the serum total soluble solids values were determined using an analytical refractometer. Total soluble solids values were corrected to *Brix values. *Brix was determined for this example and all other examples by the methods of Horwitz, W., "Official Methods of Analysis of the Association of Official Analytical Chemists", p. 363, Assn. Offic. Anal. Chem., Washington, D.C. (13th ed. 1980). Vitamin C content of all juice samples was determined using an automated 2,6-dichloroindophenol titrimetric method of the Association of Offical Analytical Chemists, 15th ed., 1990, Arlington, Va., §967.21.

TABLE 1

Improvement of Citrus fruit quality by the application of tertiary amine bioregulators. Bioregulator solutions contained 0.5% Tween 80, pH 5.0 and were applied as a single foliar treatment during early fruit development. Mature fruits were harvested 7 months after chemical treatment.

| Variety | Chemical Treatment | ml Juice per g fruit fresh wt. | Vitamin C (mg/100 ml) | Serum brix | Peel thickness (mm) |
| --- | --- | --- | --- | --- | --- |
| Kara | Control | 0.34 b | 20.6 c | 12.9 b | 4.3 b |
| | DCPTA 100 ppm | 0.38 ab | 25.2 b | 14.6 a | 3.3 a |
| | DCBTA 100 ppm | 0.42 a | 29.9 a | 14.4 a | 3.5 a |
| Kinnow | Control | 0.30 b | ND | 15.2 b | 4.7 b |
| | DCPTA 100 ppm | 0.37 a | ND | 15.3 b | 4.1 a |
| | DCBTA 100 ppm | 0.36 a | ND | 15.7 a | 4.2 a |
| Okitsu-wase | Control | 0.27 b | 24.3 b | 11.8 b | 4.6 b |
| | DCPTA 100 ppm | 0.41 a | 25.8 a | 13.1 a | 3.2 a |
| | DCBTA 100 ppm | 0.41 a | 24.8 b | 13.4 a | 3.4 a |

Letters within columns indicate mean separations according to Duncan's multiple range test, 5% level.
ND = not determined.

EXAMPLE 2

The coordinated improvement of peel structure and juice composition of citrus fruits is measured.

Citrus trees were maintained as:

a. Mature orchard trees of 'Olinda' Valencia sweet orange located at the Agricultural Experiment Station, University of California, Riverside, Calif.; and b. Orchard trees of Hamlin and Pineapple sweet orange located in Irvin, Calif.

a. Riverside Field Planting:

A 24-tree block of 'Olinda' valencia orange was assigned for bioregulator treatments. The trees were 10 years old and had been skirted. Each treatment group contained three trees. Chemical treatment groups consisted of: Control; DCPTA-50 ppm; DCPTA-100 ppm; DCBTA-50 ppm; DCBTA-100 ppm; MBTA-50 ppm; MBTA-100 ppm;

MBTA-200 ppm. All solutions (pH 5.0) contained 0.5% Tween 80 (v/v). Bioregulator solutions were applied as a single application. Each tree received 4 liters of bioregulator solution that was applied as evenly as possible to the entire foliage canopy. At the time of bioregulator treatment, fruit sizes ranged from 2 to 3.5 cm in fruit diameter. Fruits were harvested in December, six months after chemical treatment. For the December harvest, medium sized canopy fruits were randomly chosen without regard to external peel color. Fruit structure and juice composition were determined essentially as described for example 1. Fruits were juiced using a Sunkist electric hand-juicer that was fitted with a 3 mm pulp screen. Data represent three independent samples of randomly chosen fruits (eight fruits/sample).

DCPTA, 50 ppm DCBTA, and 50 ppm MBTA-treated trees generally showed the most uniform improvements in flavedo carotenoid development (FIG. 1a) when compared with control fruits. Sectioned fruits (FIG. 1c) from control and bioregulator-treated trees visually showed similar endocarp carotenoid development. However, fruits harvested from bioregulator-treated 'Olinda' trees showed significant reduction in peel thickness (FIG. 1c and Table 3).

b. San Joaquin Valley Field Trials:

Commercial orchard stock of Pineapple, Hamlin, and Valencia sweet orange were used for bioregulator experiments. Each bioregulator treatment represents one tree for each cultivar, Trees are 12 to 15 years old and have not been skirted. Experimental trees are internal plantings within a

TABLE 2

| Chemical Treatment (ppm) | Fruit Diam | ml Juice per g Fresh Fruit wt | Vitamin C (mg/100 ml) | Serum *Brix | Peel mm | Percent of Fruit Fresh wt | | |
|---|---|---|---|---|---|---|---|---|
| | | | | | | Juice | Peel + Pulp | Total |
| Control | 65.4 | 0.48 | 43.3 | 9.84 | 4.8 | 50.7 | 47.6 | 98.3 |
| DCPTA-50 | 65.1 | 0.49 | 50.6 | 11.14 | 4.3 | 51.2 | 47.1 | 98.3 |
| DCPTA-100 | 65.2 | 0.48 | 48.3 | 10.64 | 4.4 | 51.1 | 47.5 | 98.6 |
| | ns | ns | L*, Q* | L*, Q* | L* | | | |
| DCBTA-50 | 65.6 | 0.48 | 47.0 | 10.94 | 4.5 | 51.1 | 47.2 | 98.3 |
| DCBTA-100 | 65.0 | 0.49 | 47.8* | 10.65 | 4.6 | 50.9 | 47.1 | 98.0 |
| | ns | ns | L* | L* | L* | | | |
| MBTA-50 | 65.2 | 0.49 | 48.2 | 11.44 | 4.2 | 51.6 | 46.9 | 98.5 |
| NBTA-100 | 64.7 | 0.47 | 47.3 | 11.14 | 4.5 | 50.9 | 47.2 | 98.1 |
| MBTA-200 | 64.8 | 0.46 | 52.0 | 10.84 | 4.7 | 50.4 | 48.3 | 98.7 |
| | ns | ns | L* | Q* | Q* | | | | ns, *, L, Q Not significant or significant at P = 0.05(*) according to linear (L) ar quadratic (Q) models Fruit diameters and ml fruit/fresh weight remain comparable among controls and all treatment groups (Table 2). Chemical treatments show a reduction in peel thickness relative to controls, while fruit diameters are comparable for all groups including controls. However, it is notable that MBTA-50 treated exhibit at significant increase in Brix. When compared with control juice samples, chemical treatment significantly increased the Vitamin C content of Valencia sweet orange. Among all treatments, MBTA-200 ppm treatment resulted in the largest numerical increase in Vitamin C accumulation in mature fruits (Table 2).

Figure 1A:
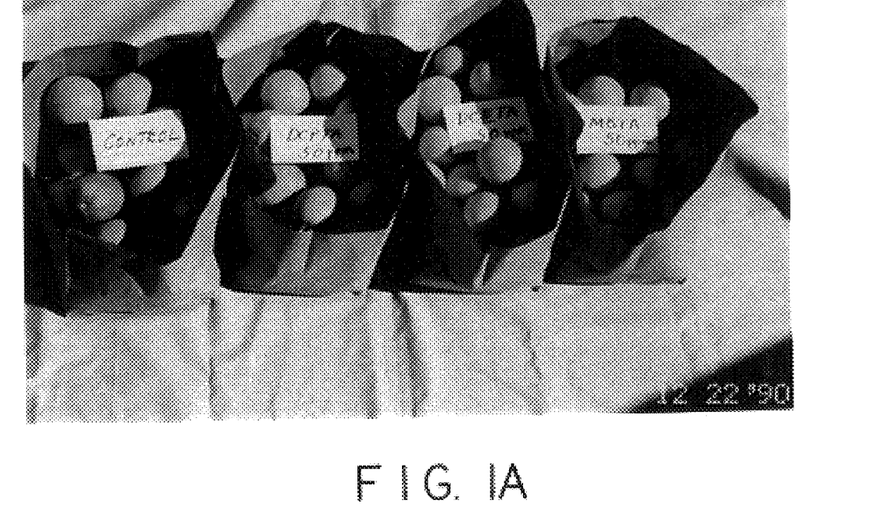
FIGS. 1a, 1b, and 1c show that bioregulator application to fruiting 'Olinda' valencia trees significantly enhanced the flavedo carotenoid accumulation of fruits that were harvested 6 months after chemical treatment.
Figure 1B:
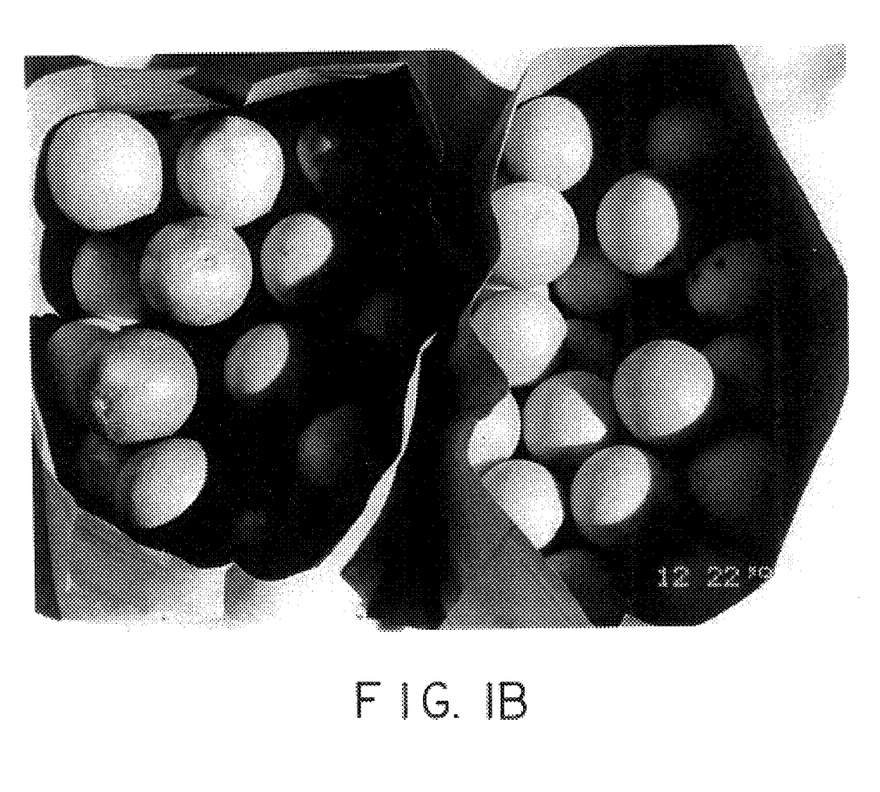
Figure 1C:
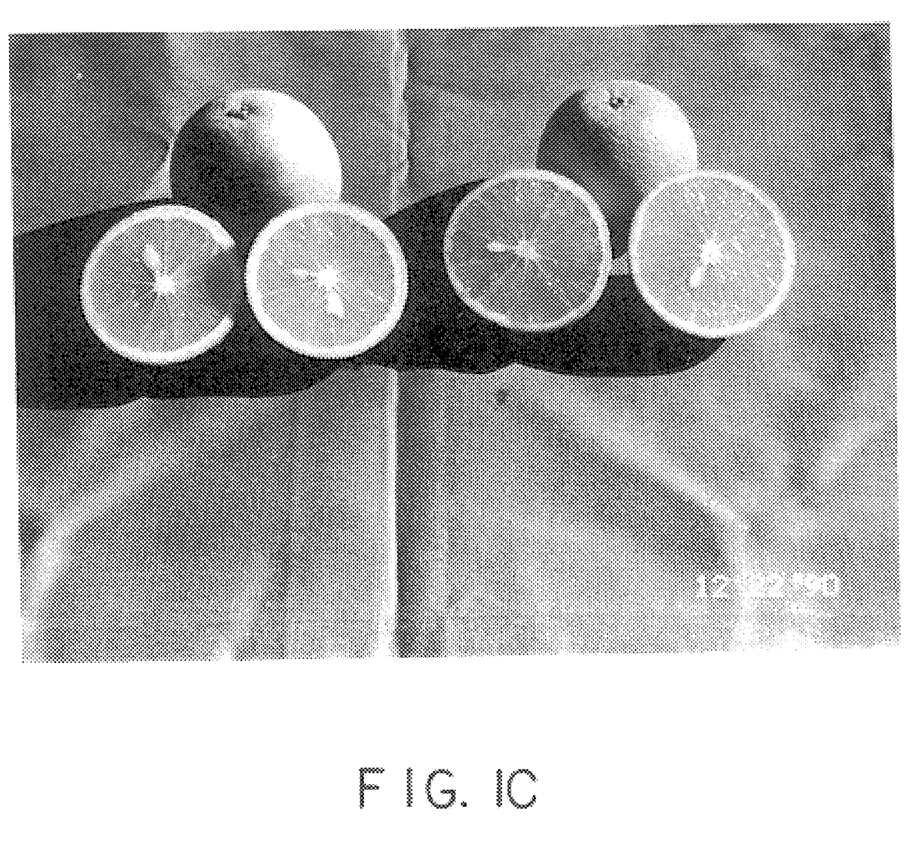

Bioregulator application to fruiting 'Olinda' valencia trees significantly enhanced the flavedo carotenoid accumulation of fruits that were harvested 6 months after chemical treatment (FIGS. 1a, 1b, 1c). Fruits harvested from 50 ppm 500 tree block. Chemical treatments were applied as a single foliar application and consisted of: Control; DCPTA-100 ppm; DCBTA-100; MBTA-100 ppm. All solutions (pH 5.0) contained 0.1% Tween 80 (v/v). Approximately 5 liters of solution were applied to each tree and the foliage canopy was covered as evenly as possible. At the time of chemical treatment, fruit sizes ranged from 1.5 to 3 cm in diameter. Mature fruits of Hamlin and Pineapple orange were harvested as part of a December harvest 6 months after chemical treatment. Fruits within all treatment groups had attained uniform peel color. Medium-sized, canopy fruits were chosen for harvest. Fruit structure and juice composition analysis were performed as described for Example 1. The data below represents eight fruits/sample.

TABLE 3

| Chemical Treatment | Fruit Diam | ml Juice per g fruit fresh wt | Vitamin C (mg/100 ml) | Serum *Brix | Peel mm | Percent of Fruit Frest Wt | | |
|---|---|---|---|---|---|---|---|---|
| | | | | | | Juice | Peel + Pulp | Total |
| HAMLIN | | | | | | | | |
| Control | 67.9a | 0.51ab | 44.8c | 11.44c | 5.1b | 52.3 | 45.3 | 97.6 |
| DCPTA-100 | 68.2a | 0.51ab | 52.5b | 11.68bc | 4.7ab | 52.4 | 46.1 | 98.5 |
| DCBTA-100 | 66.6a | 0.54a | 51.2b | 11.74b | 4.5a | 54.1 | 43.6 | 97.7 |
| MBTA-100 | 67.1a | 0.48b | 59.5a | 12.14a | 4.8b | 46.0 | 51.6 | 97.6 |
| PINEAPPLE | | | | | | | | |
| Control | 69.0a | 0.51ab | 53.1b | 11.17c | 5.6c | 49.5 | 48.4 | 97.9 |
| DCPTA-100 | 70.8a | 0.54a | 46.3c | 11.37bc | 4.7b | 55.9 | 43.3 | 99.3 |

TABLE 3-continued

| Chemical Treatment | Fruit Diam | ml Juice per g fruit fresh wt | Vitamin C (mg/100 ml) | Serum *Brix | Peel mm | Percent of Fruit Frest Wt | | |
|---|---|---|---|---|---|---|---|---|
| | | | | | | Juice | Peel + Pulp | Total |
| DCBTA-100 | 68.8a | 0.55a | 46.1c | 11.97b | 4.3a | 56.2 | 41.3 | 97.5 |
| MBTA-100 | 67.1a | 0.46b | 61.0a | 13.57a | 5.5c | 45.7 | 51.7 | 97.4 |

Letters within columns indicate mean separations according to Duncan's multiple range test, 5% level.

DCBTA shows a marked increase in juice recovery/fresh fruit weight in Hamlin and Pineapple fruits. For both Hamlin and Pineapple sweet orange, MBTA treatment shows significant improvement in brix and vitamin C content when compared with control fruits. These results indicate that MBTA-treatment resulted in sweeter fruits with an improved nutritional quality.

When compared with controls, bioregulator-mediated improvements in mature Hamlin and Pineapple sweet orange fruits showed similar trends that were observed in mature tangerine fruits (Table 1). Application of DCBTA resulted in the best juice recovery in both Hamlin and Pineapple fruits. However, MBTA foliar-application resulted in the largest numerical increase in brix and vitamin C contents when compared with the values of controls. Improved juice recovery was generally related to a reduction in peel thickness (Tables 1, 2, and 3). However, chemical treatment had no significant effect on final fruit size or fruit shape.

EXAMPLE 3

Four substituted tertiary amines (3,4-DCPTA, 3,4-DCBTA, (2,4-DCBTA), and MBTA were synthesized and purified according to the methods of Echols, Maier, Poling, and Sterling, 1981, New bioregulators of Gibberellin Biosynthesis in *Gibberella Fuiikuroi*. Phytochemistry 20:433–437; Poling, Hsu, Yokoyama, 1977 Structure. Activity Relationships of Chemical Inducers of Carotenoid Biosynthesis, Phytochemistry 14:1933, respectively. Tween 80 was purchased from Sigma Chemical Co., St. Louis, Mo.

Radish seeds (*Raphanus sativus* L. cv. Scarlet turnip white tipped) were supplied by Ferry Morse Seed Co., Modesto Calif. Seeds were soaked for 6 hrs at 22° C. in 0.1, 1.0, 10.0, 50.0, and 100.0 ppm bioregulator solutions. All bioregulator solutions (pH 5.0) contained 0.1% Tween 80. Control seed lots were soaked for 6 hrs at 22° C. in 0.1% Tween 80. Seeds were planted immediately after chemical treatment. All plants were greenhouse grown using standardized radish as described previously. Keithly, J. H., H. Kobayashi, H. Yokoyama, and H. W. Gausman 1991 Promotive Effects of Tertiary Amine Bioregulators on Radish (Raphanus sativus) Growth and Development. PGRSA Quarterly 19(3): 182–187.

The growth enhancing properties of the newly synthesized tertiary amine analogs showed significant differences in a standardized radish growth test (Table 4). The growth of nontreated controls and of DCPTA-treated plants were used as reference plant growth systems.

The growth of DCBTA-treated plants were numerically and statistically similar to the growth of DCPTA-treated plants. Both compounds showed significant quadratic responses for leaf and root development. Within the DCBTA-treatments leaf and root growth were maximized using a 10 ppm seed-treatment.

Among all chemical treatments, the taproot growth of 50 ppm MBTA-treated plants showed the largest numerical increase when compared to growth of controls. The dose-response characteristics of MBTA-treated plants showed significant quadratic responses for leaf and taproot growth. The leaf growth of MBTA-treated plants was numerically similar to the leaf growth of DCPTA-treated plants.

Of the compounds tested, MBTA-treated plants showed the largest improvements in radish taproot development when compared with the growth of controls. The significant quadratic model response of MBTA-treated plants suggests that 50 ppm may be preferred for plant growth. When compared to the taproot growth of DCPTA-treated plants, the order of compound effectiveness appears to be as follows:

MBTA>3,4-DCBTA=DCPTA>>2,4-DCBTA

TABLE 4

Enhanced Leaf and Taproot Growth of Radish by Tertiary-amine Bioregulators

| Bioregulator Abbreviation | Conc ppm | Leaf Dry wt g | Leaf Area $dm^2$ | Root Dry wt g | Root Diam mm | Root to Shoot Ratio |
|---|---|---|---|---|---|---|
| Control | | 1.04 | 2.64 | 0.82 | 22.89 | 0.79 |
| 3,4-DCPTA | 0.1 | 1.18 | 2.72 | 1.10 | 23.40 | 0.86 |
| | 1.0 | 1.58 | 3.64 | 1.29 | 27.59 | 0.82 |
| | 10.0 | 1.38 | 3.19 | 1.32 | 30.09 | 0.96 |
| | 50.0 | 1.21 | 2.79 | 1.17 | 25.32 | 0.97 |
| | 100.0 | 1.00 | 2.31 | 1.06 | 23.82 | 1.06 |
| | | Q* | Q** | Q* | Q** | L* |
| 3,4-DCBTA | 0.1 | 1.22 | 3.11 | 1.02 | 22.54 | 0.84 |
| | 1.0 | 1.25 | 3.15 | 0.97 | 21.44 | 0.78 |
| | 10.0 | 1.48 | 3.89 | 1.33 | 29.38 | 0.90 |
| | 50.0 | 1.19 | 3.09 | 1.02 | 22.71 | 0.86 |

TABLE 4-continued

Enhanced Leaf and Taproot Growth of Radish by Tertiary-amine Bioregulators

| Bioregulator Abbreviation | Conc ppm | Leaf Dry wt g | Leaf Area $dm^2$ | Root Dry wt g | Root Diam mm | Root to Shoot Ratio |
|---|---|---|---|---|---|---|
| | 100.0 | 1.20 | 3.11 | 1.09 | 23.13 | 0.91 |
| | | Q* | Q** | Q* | Q* | NS |
| 2,4-DCBTA | 1.0 | 1.37 | $ND^Z$ | 1.04 | ND | 0.76 |
| | 10.0 | 1.39 | ND | 1.08 | ND | 0.78 |
| | 100.0 | 1.28 | ND | 1.12 | ND | 0.88 |
| | | Q* | | NS | | NS |
| MBTA | 0.1 | 1.15 | 2.85 | 1.01 | 22.61 | 0.88 |
| | 1.0 | 1.19 | 2.98 | 1.22 | 26.95 | 1.02 |
| | 10.0 | 1.54 | 3.08 | 1.27 | 27.61 | 0.83 |
| | 50.0 | 1.44 | 3.14 | 1.46 | 29.01 | 1.01 |
| | 100.00 | 1.12 | 2.78 | 0.92 | 22.42 | 0.82 |
| | | Q** | Q** | Q* | Q* | NS |

NS, Q*, Q**, L* Not significant or significant at P = 0.05(*) or P-0.01(**) according to linear (L) or Quadratic(Q) models.
$^Z$Not determined

EXAMPLE 4

Mesophyll chloroplast development during leaf expansion has been shown to regulate the amount of photosynthate available for vegetative crop growth and reproductive plant development. Fruit set and crop yield are often determined by the amounts of partitioned photosynthate that are available during early fruit growth. This example shows the results of a study which examined the effects of DCPTA, DCBTA, and MBTA on chlorophyll accumulation and Rubisco activity in mature leaves of Valencia, Pineapple, and Hamlin sweet oranges.

DCPTA, DCBTA, and MBTA was synthesized and purified by the methods of Poling et al. (1977) and Echols et al. (1981), respectively. All other chemicals were purchased from Sigma, Chemical Co., St. Louis, Mo.

One year old grafted trees of Valencia, Pineapple, and Hamlin sweet orange were provided by Willits and Newcomb, Inc., Arvin, Calif. Trees were planted into 15 liter plastic pots and were greenhouse-grown under a photosynthetic photon flux density 1200 to 1400 $\mu$mol $m^{-2}$ $s^{-1}$ photosynthetically active radiation. Photoperiod was extended to 12 hrs using metal halide lamps. Greenhouse temperature control was maintained at 30±4° C. day and 22±2° C. night temperatures. Plants were fertilized every 12 to 14 days with a 20N-20P-20K soluble fertilizer.

Chemical treatments were performed when a majority of the trees had started a vegetative growth cycle (growth flush) during April, 1990. Bioregulator solutions (pH 5.0) contained 0.5% Tween 80. Citrus cultivars were divided into treatment groups that contained three trees per treatment. Foliar applications of DCPTA-50 ppm, DCPTA-100 ppm, (3,4)-DCBTA-50 ppm, (3,4)-DCBTA-10 ppm, MBTA-50 ppm, and MBTA-100 ppm were performed using a trigger-action hand sprayer. Controls received a foliar application of 0.5% Tween 80. Solutions were applied to the point of foliage runoff. After chemical treatment, trees were arranged as a completely randomized block.

Leaf growth analysis was performed at 6 to 8 weeks after chemical treatment. Individual leaves were harvested from 3 vegetatively similar branches within each treatment group for leaf morphology analysis. Leaves were numbered basipetally from the first visible leaf at the apical meristem. For each leaf, leaf area ($dm^2$), leaf blade length at the midvein, and leaf fresh weight was determined. Specific leaf weights (SLW, g fresh weight/$dm^2$ leaf area) were calculated from leaf fresh weight and leaf area data.

Maximum chlorophyll and Rubisco activity were recovered from leaves numbers 15 through 18 numbered basipetally from the apical meristem. Leaf area development of harvested leaves was approximately 50 to 80% of total leaf blade expansion. For pigment and Rubisco activity determinations, five leaves were harvested from each chemical treatment group. For each leaf, chlorophyll and total carotenoids were extracted into acetone (100%) and were quantified spectrophotometrically according to the methods of Lichtenthaler (1987). Five replicate leaves were pooled for Rubisco activity determinations. Rubisco activity in leaf extracts was determined using a $[14_C]CO_2$ fixation method according to Keithly et al. (1990) with the addition of 5% polyvinylpyrrolidone to the grinding buffer. The soluble protein content of leaf extracts was determined according to the methods of Bradford (1976) using bovine gamma globulin as a protein standard. Analysis of variance was performed for all pigment, leaf morphology, and enzyme activity data. Mean separations were determined using Duncan's multiple range test, at the 5% level (Zar, 1972).

When compared with controls, foliar application of DCPTA, DCBTA, and MBTA to Valencia, Pineapple, and Hamlin sweet orange significantly increased the SLW of mature leaves that were harvested at 6 to 8 weeks after chemical treatment (Table 5). Among the bioregulator treatment groups, SLW was numerically similar. Within the three orange cultivars that were tested, bioregulator-treatments did not appear to alter the size of mature leaves (data not presented). Bioregulator application significantly (P=0.05) increased Chl accumulation in mature orange leaves when compared with that of controls. Total Chl accumulation in leaves harvested from 50 ppm bioregulator treatment groups were numerically increased over mean total Chl accumulation in 100 ppm bioregulator-treated leaves. When compared with controls, bioregulator treatment resulted in generally improved total carotenoid accumulation in mature leaves. Rubisco activity was measured in a wide range of leaf ages, and the most reliable enzyme activities were obtained from leaf numbers 15 to 18 basipetally from the apical meristem. Bioregulator treatment appeared to increase the CCS of sweet orange (Table 6). In all orange cultivars, the soluble protein to Chl ratio was increased significantly (P=0.05) in all chemical treatment groups when compared with controls. Within the chemical treatment groups, the soluble protein to Chl ratios of 50 ppm treatments often appeared to be superior to 100 ppm treatments. When compared with controls, the observed improvements in leaf soluble protein to Chl ratios, within the chemical treatment groups supported a significantly (P=0.05) increased Rubisco activity per mg Chl (Table 6). Within all treatment groups among all cultivars, 50 ppm MBTA application appeared to be one of the most useful chemical treatments. Rubisco activity was not determined in all treatment groups due to the limited amount of experimental material.

The in vitro Rubisco analysis suggests that MBTA may be a very effective chemical regulator of chloroplast development.

TABLE 5

Enhanced pigment accumulation of sweet orange leaves by tertiary-amine bioregulators

| Cultivar | Bioregulator Treatment-PPM | SLW$^z$ g/dm$^2$ | CH1 a | Ch1 b | Ch1 Total | Pigments mg/dm$^2$ Car Total |
|---|---|---|---|---|---|---|
| Valencia | Control | 2.60c | 4.0d | 1.6d | 5.6c | 1.3d |
| | DCPTA-50 | 3.01ab | 5.4b | 2.7a | 8.1a | 2.0a |
| | DCPTA-100 | 2.95b | 5.1c | 2.3bc | 7.4b | 1.7c |
| | DCBTA-50 | 3.04a | 5.ab | 2.5b | 8.1a | 1.8b |
| | DCBTA-100 | 3.02ab | 5.5b | 2.5b | 8.0a | 1.8b |
| | MBTA-50 | 2.99b | 5.7a | 2.1c | 7.8ab | 1.8b |
| | MBTA-100 | 3.05a | 5.1c | 2.1c | 7.2b | 1.8b |
| Pineapple | Control | 2.66c | 4.7b | 1.7de | 6.5c | 1.4c |
| | DCPTA-50 | 3.29ab | 4.9b | 2.5b | 7.4b | 1.4c |
| | DCPTA-100 | 3.47a | 4.0c | 1.5e | 5.5d | 1.7a |
| | DCBTA-50 | 3.18b | 5.6a | 2.1c | 7.7a | 1.5b |
| | DCBTA-100 | 2.96b | 5.2ab | 2.0d | 7.2b | 1.4c |
| | MBTA-50 | 3.49a | 4.7a | 2.8a | 7.5a | 1.6a |
| | MBTA-100 | | | NOT DETERMINED | | |
| Hamlin | Control | 2.33d | 3.9d | 1.5c | 5.4e | 1.4d |
| | DCPTA-50 | 2.72bc | 4.9b | 1.8b | 6.7c | 1.7c |
| | DCPTA-100 | 2.65c | 4.6c | 1.8b | 6.4d | 1.6c |
| | DCBTA-50 | 2.81b | | NOT DETERMINED | | |
| | DCBTA-100 | 2.79b | 5.1b | 2.2a | 7.3b | 1.7b |
| | MBTA-50 | 3.04a | 5.2a | 2.5a | 7.7a | 1.8a |
| | MBTA-100 | 2.77b | | NOT DETERMINED | | |

$^z$Specific leaf weight (g fresh weight/dm$^2$). Determined on leaf numbers 15 to 18 numbered basipetally from the apical meristem. Letters within columns indicate significant differences (cultivars analyzed separately) according to Duncan's multiple range test, 5% level.

TABLE 6

Enhanced soluble protein accumulation and Rubisco activity of sweet orange leaves by tertiary-amine bioregulators

| | Soluble Protein | Total Activated Rubisco Activity | |
|---|---|---|---|
| Treatment | To Ch1 ratio$^z$ | Activity/mg protein | Activity/mg Ch1 |
| VALENCIA | | | |
| Control | 14.52d | 2.83a | 41.09d |
| DCPTA-50 | 15.99ab | 2.81a | 44.93b |
| DCPTA-100 | 15.63c | 2.82a | 44.08c |
| DCBTA-50 | 15.95ab | 2.84a | 45.30ab |
| DCBTA-100 | 15.92ab | 2.78a | 44.26c |
| MBTA-50 | 16.24a | 2.84a | 46.12a |
| MBTA-100 | 15.86ab | 2.83a | 44.90b |
| PINEAPPLE | | | |
| Control | 15.65c | 2.83a | 44.29c |
| DCPTA-50 | 16.33a | 2.78a | 45.40a |
| DCPTA-100 | NOT DETERMINED | | |
| DCBTA-50 | 16.21a | 2.77a | 44.90b |
| DCBTA-100 | 15.90b | 2.80a | 44.52c |
| MBTA-50 | 16.19ab | 2.81a | 45.49a |
| MBTA-100 | NOT DETERMINED | | |
| HAMLIN | | | |
| Control | 14.92c | 2.77a | 41.33d |
| DCPTA-50 | 15.98b | 2.82a | 45.06c |
| DCPTA-100 | 16.01b | 2.79a | 44.67c |
| DCBTA-50 | 16.92a | 2.83a | 47.88a |

TABLE 6-continued

Enhanced soluble protein accumulation and Rubisco activity of sweet orange leaves by tertiary-amine bioregulators

| | Soluble Protein | Total Activated Rubisco Activity | |
|---|---|---|---|
| Treatment | To Ch1 ratio$^z$ | Activity/mg protein | Activity/mg Ch1 |
| DCBTA-100 | 16.74a | 2.80a | 46.87b |
| MBTA-50 | 16.40ab | 2.83a | 46.41b |
| MBTA-100 | NOT DETERMINED | | |

$^z$mg protein/(mg Ch1) in Citrus leaf chloroplast preparations
$^y$Rubisco activity = mg $CO_2$/h. Letters within columns indicate mean separations according to Duncan's multiple range test, 5% level.

EXAMPLE 5

Orchard trees of 'Olinda' Valencia orange were maintained at the Agricultural Experiment Station, University of California, Riverside, Calif. Twenty four trees were treated with tertiary amine bioregulators as foliage treatments. Each treatment group contained three trees. The randomized complete block experimental design contained the following bioregulator treatments: Control; DCPTA-50 ppm; DCPTA-100 ppm; DCBTA-50 ppm; DCBTA-100 ppm, MBTA-50 ppm; MBTA-100 ppm; and MBTA-200 ppm. All bioregulator solutions (pH 5.0) contained 0.1% Tween 80 (v/v). Fruits were harvested at 181 days, 215 days, and 259 days after bioregulator treatment (DAT). Sized fruits were analyzed for peel thickness, juice recovery, juice brix, and total peel pigment accumulation. Each fruit sample contained eight randomly chosen fruits. Each were juiced using a Sunkist electric juicer that was fitted with a 3 mm pulp screen. Total soluble solids (*Brix) of juice samples was determined by analytical refractometry. Three independent peel samples were extracted into methanol. Total chlorophylls (Chl a and Chl b) and total carotenoids (xanthophylls and carotenes) were quantified using the spectrophotometric extinction coefficients of Lichtenthaler (1987). Separations among mean values were determined according to Duncan's multiple range test, at the 5% level.

Figure 2:
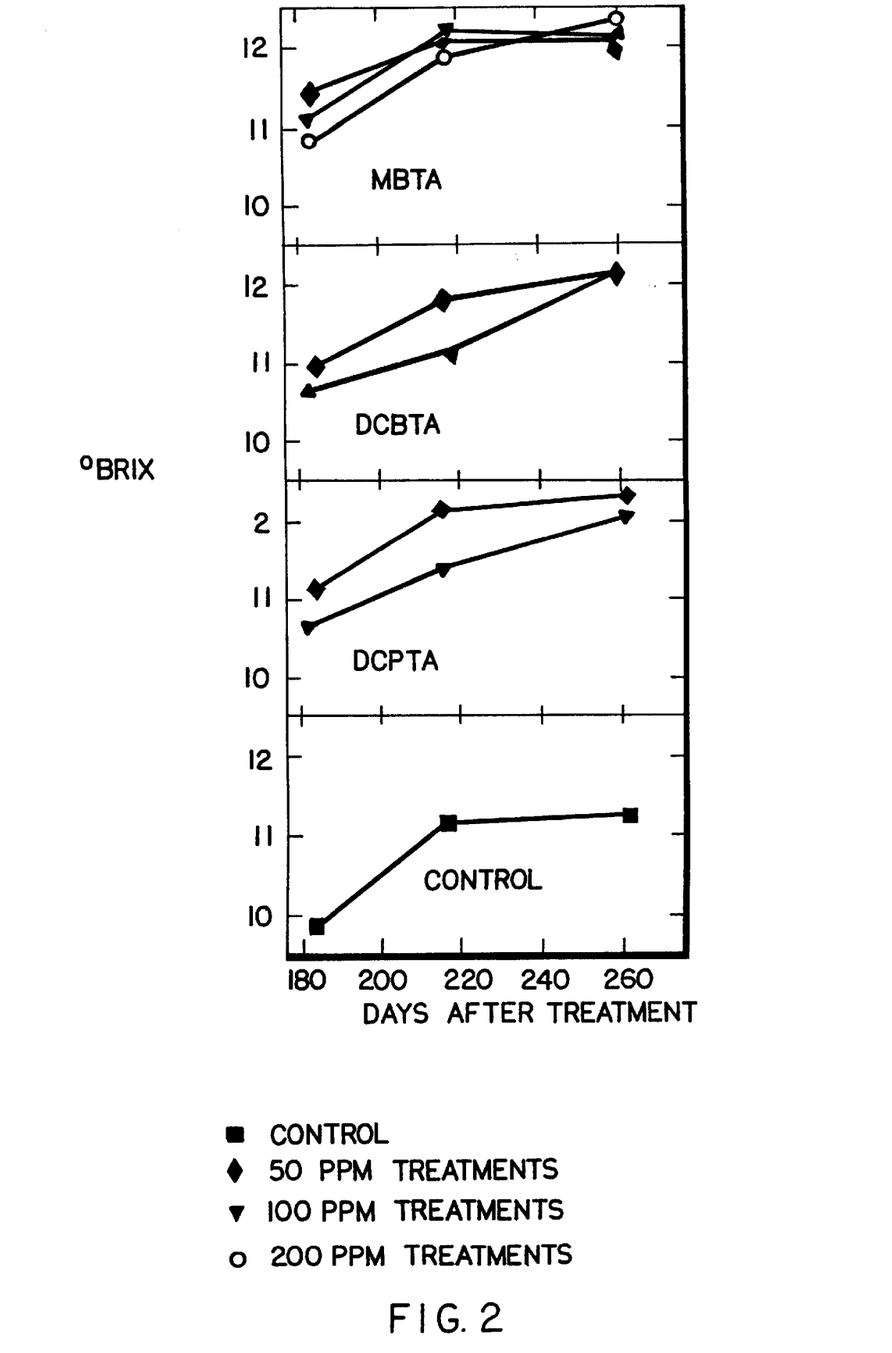
FIG. 2 shows that among three fruit harvests, total soluble solids (brix) accumulation in treated fruits was increased significantly as compared with controls.

Compared with controls, fruits harvested from bioregulator-treated 'Olinda' trees showed improved peel development and juice accumulation during fruit maturation (Table 7). All fruits harvested from bioregulator-treated trees showed a general reduction in peel thickness as compared with the peel development of controls. Within chemical treatment groups, 50 ppm treatments generally appeared to be the most useful treatments to reduce peel thickness. As fruit development progressed, the juice recovery of all chemical treatments increased significantly as compared with the juice accumulation of controls. However, among the 215 and 259 DAT harvests, no specific dose-response trends were observed within the chemical treatments. Among the three fruit harvests, total soluble solids (brix) accumulation in treated fruits was increased significantly as compared with controls (FIG. 2). Due to excessively cold weather from 220 to 260 DAT, sugar accumulation in fruits harvested from control trees was greatly reduced during this time period. However, fruits harvested from 100 ppm DCPTA, 100 ppm DCBTA, and 200 ppm MBTA-treated trees showed a significantly increased solids accumulation during 220 to 260 DAT.

Fruits harvested from bioregulator-treated trees showed significant improvements in peel pigment accumulation when compared with controls (Table 8). Among all treatments, chlorophyll content was inversely related to total carotenoid content. The biological activities of DCBTA and MBTA on carotenoid accumulation appeared greater than that of DCPTA. Among all treatments, the largest numerical enhancement of carotenoid accumulation was observed within the 50 ppm MBTA-treatment.

The brix and carotenoid accumulation of 'Olinda' fruits harvested from bioregulator-treated trees indicates that chemical treatment has reduced the days to fruit harvest by approximately 40 days when compared with controls. Among all treatments, improved juice recovery is related to a reduction in peel thickness. In general, 50 ppm treatments appear to be the most useful to promote fruit structure and composition improvements during fruit growth and maturation. Of the test bioregulators, MBTA appears to have the greatest biological activity on carotenoid accumulation. At 259 DAT, fruits harvested from 50 ppm MBTA-treated trees showed a 68% increase in carotenoid content, a 10% increase in brix, and an 8% increase in juice recovery when compared with the values of controls.

TABLE 7

Enhanced juice recovery and reduced peel thickness of Valencia sweet orange by tertiary-amine bioregulators

| | DAYS AFTER BIOREGULATOR TREATMENT | | |
|---|---|---|---|
| | 181 | 215 | 259 |
| Fruit Size (mm) | 65.1 ± 0.3 | 64.8 ± 0.7 | 67.1 ± 0.6 |
| Juice Recovery (ml juice/fresh wt) | | | |
| Control | 0.48a | 0.47b | 0.51b |
| DCPTA-50 | 0.49a | 0.53a | 0.53ab |
| DCPTA-100 | 0.48a | 0.49b | 0.57a |
| DCBTA-50 | 0.48a | 0.50ab | 0.53ab |
| DCBTA-100 | 0.49a | 0.50ab | 0.53ab |
| MBTA-50 | 0.49a | 0.50ab | 0.55a |
| MBTA-100 | 0.47a | 0.51a | 0.55a |
| MBTA-200 | 0.46a | 0.52a | 0.54ab |
| Peel Thickness (mm) | | | |
| Control | 4.8b | 5.0c | 4.9c |
| DCPTA-50 | 4.3a | 4.4b | 4.5bc |
| DCPTA-100 | 4.4ab | 4.5b | 4.2b |
| DCBTA-50 | 4.5ab | 4.4b | 4.4b |
| DCBTA-100 | 4.6b | 4.5b | 4.4bc |
| MBTA-50 | 4.2a | 4.0a | 3.8a |
| MBTA-100 | 4.5ab | 4.4b | 4.2b |
| MBTA-200 | 4.7b | 4.4b | 4.3b |

Letters within columns indicate mean separations according to Duncan's multiple range test, 5% level.

TABLE 8

Enhanced pigment accumulation of Valencia sweet orange by tertiary-amine bioregulators

| | DAYS AFTER BIOREGULATOR TREATMENT | | |
|---|---|---|---|
| | 181 | 215 | 259 |
| Total Chlorophylls Control | 0.60c | 0.47c | 0.41b |
| DCPTA-50 | 0.27b | 0.19b | 0.17ab |
| DCPTA-100 | 0.21ab | 0.18b | 0.12a |
| DCBTA-50 | 0.20ab | 0.19b | 0.14a |
| DCBTA-100 | 0.16a | 0.15ab | 0.12a |
| MBTA-50 | 0.23b | 0.14ab | trace |
| MBTA-100 | 0.10a | 0.12a | 0.12a |
| MBTA-200 | 0.22ab | 0.15ab | 0.11a |
| Total Carotenoids Control | 2.07d | 2.99c | 3.46c |
| DCPTA-50 | 2.35c | 4.00b | 4.31b |
| DCPTA-100 | 2.28c | 4.27b | 4.83ab |
| DCBTA-50 | 2.71ab | 5.01ab | 5.46a |
| DCBTA-100 | 2.86ab | 4.87ab | 5.55a |
| MBTA-50 | 3.05a | 5.43a | 5.82a |
| MBTA-100 | 2.64b | 4.99ab | 5.77a |
| MBTA-200 | 2.85ab | 4.92ab | 5.41a |

Letters within columns indicate mean separations according to Duncan's multiple range test, 5% level.

We claim:

1. N,N-diethylaminoethyl 2,4-dichlorobenzyl ether.
2. N,N-diethylaminoethyl 3,4-dichlorobenzyl ether.

* * * * *